(12) United States Patent
Tornier

(10) Patent No.: US 6,206,925 B1
(45) Date of Patent: Mar. 27, 2001

(54) ELBOW PROSTHESIS WITH INDEXED SPHERE

(75) Inventor: Alain Tornier, St Ismier (FR)

(73) Assignee: Tornier SA, Saint Ismier (FR)

( * ) Notice: Subject to any disclaimer, the term of this patent is extended or adjusted under 35 U.S.C. 154(b) by 0 days.

(21) Appl. No.: 09/151,205

(22) Filed: Sep. 11, 1998

(30) Foreign Application Priority Data

Sep. 12, 1997 (FR) .................................... 97 11603

(51) Int. Cl.⁷ .................................................. A61F 2/36
(52) U.S. Cl. .................................................. 623/19.12
(58) Field of Search ..................... 623/18, 23, 19.11, 623/19.12

(56) References Cited

U.S. PATENT DOCUMENTS

| 5,358,526 | 10/1994 | Tornier . |
| 5,702,457 | 12/1997 | Tornier . |
| 5,741,335 | 4/1998 | Gerber et al. . |

FOREIGN PATENT DOCUMENTS

| 19509037 | 9/1996 | (DE) . |
| 0549480 | 6/1993 | (EP) . |
| 0639359 | 2/1995 | (EP) . |
| 0679375 | 11/1995 | (EP) . |
| 0712617 | 5/1996 | (EP) . |
| 0715836 | 6/1996 | (EP) . |
| 2685633 | 7/1993 | (FR) . |
| 2727002 | 5/1996 | (FR) . |
| WO 96/17553 | 6/1996 | (WO) . |
| WO 97/25943 | 7/1997 | (WO) . |

Primary Examiner—Michael Milano
(74) Attorney, Agent, or Firm—Greenblum & Bernstein, P.L.C.

(57) ABSTRACT

Humeral prosthesis having a rod for anchoring into a humeral canal of a humerus. The prosthesis has a hemispherical cup adapted to engage a shoulder socket and a connection which connects the rod to the hemispherical cup. The connection includes a spherical portion and the spherical portion includes a spherical engaging surface having at least one recess. At least one reference mark is disposed on at least one of the rod, the hemispherical cup, and the connection. The at least one reference mark corresponds to the at least one recess. The prosthesis also has a binding mechanism for engaging the at least one recess. The hemispherical cup is pivotal about the spherical portion and fixable in a finite number of combined angular positions which correspond to a number of recesses.

31 Claims, 6 Drawing Sheets

ELBOW PROSTHESIS WITH INDEXED SPHERE

CROSS-REFERENCE TO RELATED APPLICATIONS

The present application claims priority under 35 U.S.C. § 119 of French Patent Application No. FR 97 11603, filed on Sep. 12, 1997.

BACKGROUND OF THE INVENTION

1. Field of the Invention

The present invention relates to improvements made to sphere-type shoulder prostheses of the kind which comprise a rod which is anchored into the humeral canal and a hemispherical cup which can interact with the shoulder socket.

The prosthesis according to the invention, which may or may not be associated with a prosthetic socket, allows for the surgical treatment of degenerative afflictions of gleno-humeral arthrosis, and also of other afflictions. Furthermore, the prosthesis according to the invention is also intended for cephalo-tuberosital fractures which are not accessible to conservative surgery, and also to any painful syndrome of the shoulder.

2. Description of Background and Relevant Information

French patent application No. 2 727 002 of which the present applicant is proprietor discloses a humeral prosthesis with a sphere comprising, in the metaphyseal region of the humeral rod, a cylindrical housing with a spherical end into which a sphere designed to receive a hemispherical cup is inserted, while binding means allow these to be immobilized in a determined position with respect to the axis of the rod.

Also, French patent application No. 2 685 633 of which the applicant is proprietor discloses a modular humeral prosthesis made up of three elements one of which is an anchoring rod provided with a metaphyseal region formed of an oblique bearing face. The second element is a distance piece in the form of a wedge, one of the end faces of which fits on the bearing face of the rod. The third element of the prosthesis is a hemispherical cup, the base of which is fixed with respect to the second end face of the distance piece. This attachment, which is offcentered with respect to the geometric axis of the cup, allows for angular adjustment of the latter with respect to the distance piece.

Such prostheses have certain drawbacks regarding the systems for immobilizing the spheres, which are inaccessible once the prostheses have been inserted into the humeral canal, because the binding screws are located inside the bone cavity.

Furthermore, it can be observed that, because a sphere is being used, there are an infinite number of relative positions between rod and sphere, and this makes reproducing on the implant the geometry measured using the test piece impossible.

SUMMARY OF THE INVENTION

The improvements which are the subject of the present invention aim to allow a humeral prosthesis to be produced which overcomes the above drawbacks.

The humeral prosthesis with a sphere, comprising a rod which can be anchored into the humeral canal, a hemispherical cup which can interact with the shoulder socket and a sphere providing the connection between the rod and the cup, and provides for indexing the sphere and/or the cup with respect to the rod in a finite number of combined angular positions $\alpha$ and $\beta$ of the cup with respect to the rod, which positions are obtained from measurements read off from a test piece or some other method in order, using binding mechanisms, to immobilize the sphere and/or the cup on the rod before it is fitted in the humeral canal, the angles $\alpha$ and $\beta$ respectively representing the angle of inclination in the frontal plane, and the anteversion or retroversion angle of inclination with respect to the frontal plane about the axis of the rod. [sic]

The humeral prosthesis comprises a combination of a fixed pointer with a reference mark and a recess opposite the axis of the hole which allows the angles $\alpha$ and $\beta$ to be reproduced.

The humeral prosthesis comprises a hole that receives the binding mechanisms which is located along an axis that does not run through the center of the sphere and/or the cup so as to prevent any relative movement between the sphere and/or the cup with respect to the rod.

The humeral prosthesis comprises a rod which in its metaphyseal region comprises a cavity capable of accommodating a sphere interacting with the cup, while binding mechanisms provided on the rod allow the sphere and the cup to be immobilized.

The humeral prosthesis comprises a rod which in its metaphyseal region is secured to a sphere which interacts with a housing formed in the cup, while binding mechanisms provided on the cup allow it to be immobilized on the sphere.

The humeral prosthesis comprises a rod which in its metaphyseal region comprises a housing in the middle of which there is drilled a hole with a tapering profile receiving a peg of the same profile extending from a flange placed in the housing, the flange being secured, on the opposite side from the peg, to a sphere which interacts with the housing provided in the cup.

The humeral prosthesis comprises an axis of the sphere which is laterally offset by a distance with respect to the axis of the flange, so as to allow the cup to be offcentered.

BRIEF DESCRIPTION OF THE DRAWINGS

The description which will follow with reference to the appended drawings, given by way of nonlimiting examples, will allow a better understanding of the invention, its features and the advantages it is able to afford.

DETAILED DESCRIPTION OF THE INVENTION

Figure 1:
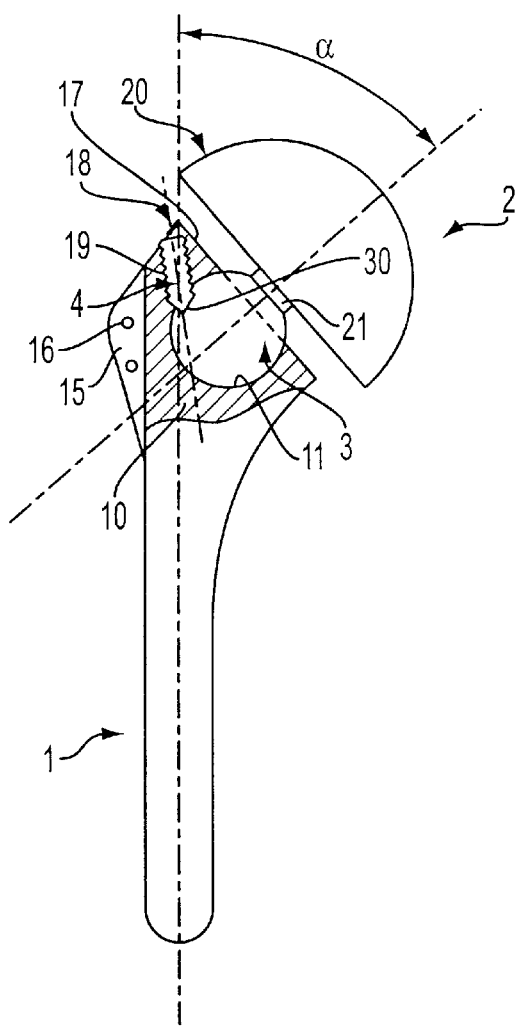
FIG. 1 is a frontal view depicting the humeral prosthesis according to the present invention in a first angular position $\alpha$ of the cup with respect to the rod of the prosthesis.
Figure 2:
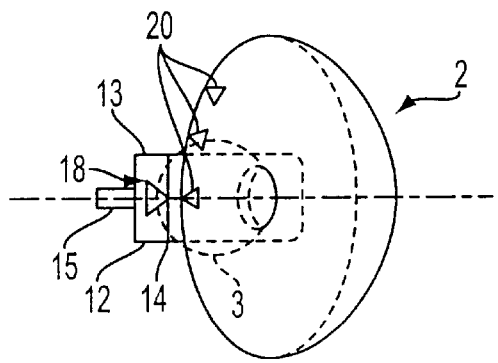
FIG. 2 is a view from above showing the humeral prosthesis in its angular position of FIG. 1.
Figure 3:
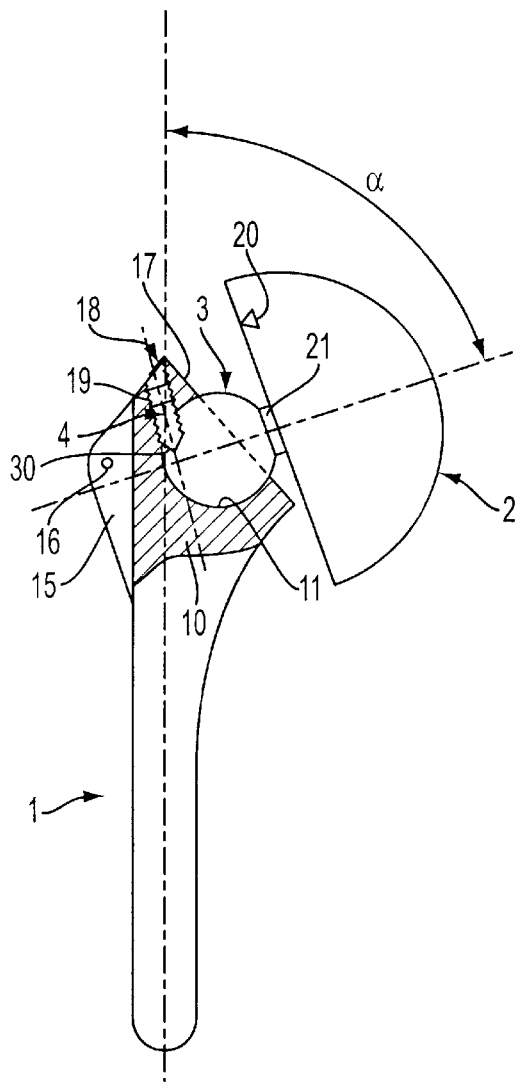
FIG. 3 is a frontal view illustrating the humeral prosthesis in a second angular position $\alpha$ of the cup with a different value than the one provided in FIG. 1, of the cup with respect to the rod of the prosthesis.
Figure 4:
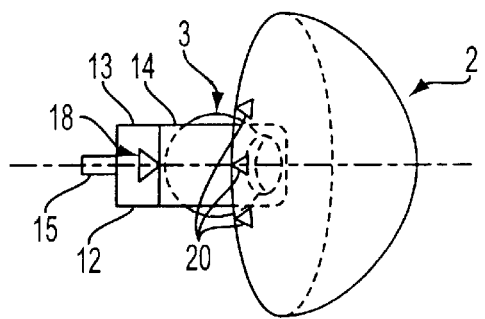
FIG. 4 is a view from above showing the humeral prosthesis according to the present invention, in its angular position of FIG. 2 [sic].
Figure 5:
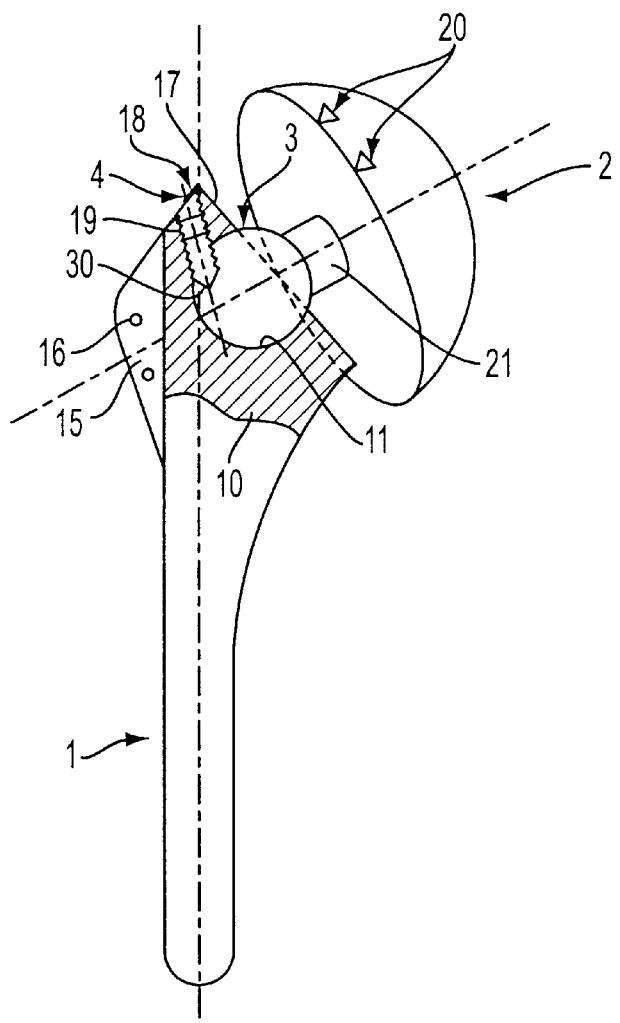
FIG. 5 is a frontal view depicting the humeral prosthesis in a third angular position.
Figure 6:
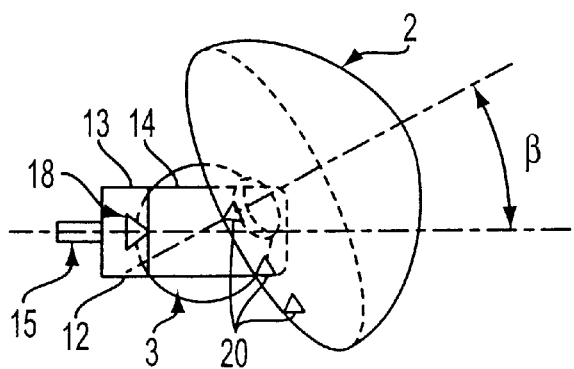
FIG. 6 is a view from above illustrating the humeral prosthesis in its angular position of FIG. 5, at an angle $\beta$ with respect to the frontal plane of the rod of the prosthesis.

Depicted in FIGS. 1 to 6 are the three elements of the humeral prosthesis according to the invention, namely a rod 1 that can be anchored into the humeral canal, a hemispherical cup 2 capable of interacting with the shoulder socket and a sphere 3 providing the mechanical link between the rod 1 and the cup 2.

The rod 1 is of cylindrical section comprising a metaphyseal region 10, with a flared profile, which has a cavity 11 in which the sphere 3 engages. In the sagittal plane, the metaphyseal region 10 has straight and parallel panels 12 and 13 defining its thickness. Note that the thickness of the metaphyseal region 10 is smaller than the diameter of the sphere 3. This is because the panels 12 and 13 can each be pierced with a hole or cut-out 14 opening into the cavity 11 and allowing the poles of the sphere 3 to protrude outward.

The metaphyseal region 10 has one or more fins 15 which are arranged on the external and/or lateral face of the rod 1, while perforations 16 are formed in the fins 15 to allow the upper end of the humerus to be reconstructed around the prosthesis in the event of fracture.

The rod 10 terminates in a face 17 which is inclined with respect to the longitudinal axis of the rod. The rod 10 comprises a fixed pointer 18 which may, for example, be embodied by the fin 15 or any other mechanisms.

The exterior profile of the cup 2 has graduations or reference marks 20 which correspond to recesses 30 formed on the surface of the sphere 3 so that the latter can be perfectly positioned with respect to the rod 1 according to the measurements taken from a test piece.

Between the fin 15 and the inclined face 17, the metaphyseal region 10 is pierced with a tapped hole 19 which opens into the cavity 11 to allow the sphere 3 to be immobilized, using a screw 4, in a position that is determined using the pointer 18 and the reference marks 20.

The binding screw 4 interacting with the hole 19 enters the sphere 3 along an axis that does not run through the center of the sphere, and this prevents any relative movement of the sphere 3 with respect to the rod 1.

It can be seen that the axis of the hole 19 is slightly inclined with respect to the vertical axis of the rod 1 so as to allow the screw 4 always to be accessible when the prosthesis is introduced into the humeral canal.

Note that the combination of a pointer 18 with a reference mark 20 and a recess 30 facing the axis of the hole 19 reproduces a previously measured combined angular position of the angles α and β, measured for example from the test piece.

The sphere 3 is intended to be solid and connected directly to the cup 2 by a pin 21, the length of which can vary depending on the pathological case. This structure entails having in stock a certain number of spheres 3 secured to their cup 2 in order to be able to cater for all operating scenarios.

Figure 7:
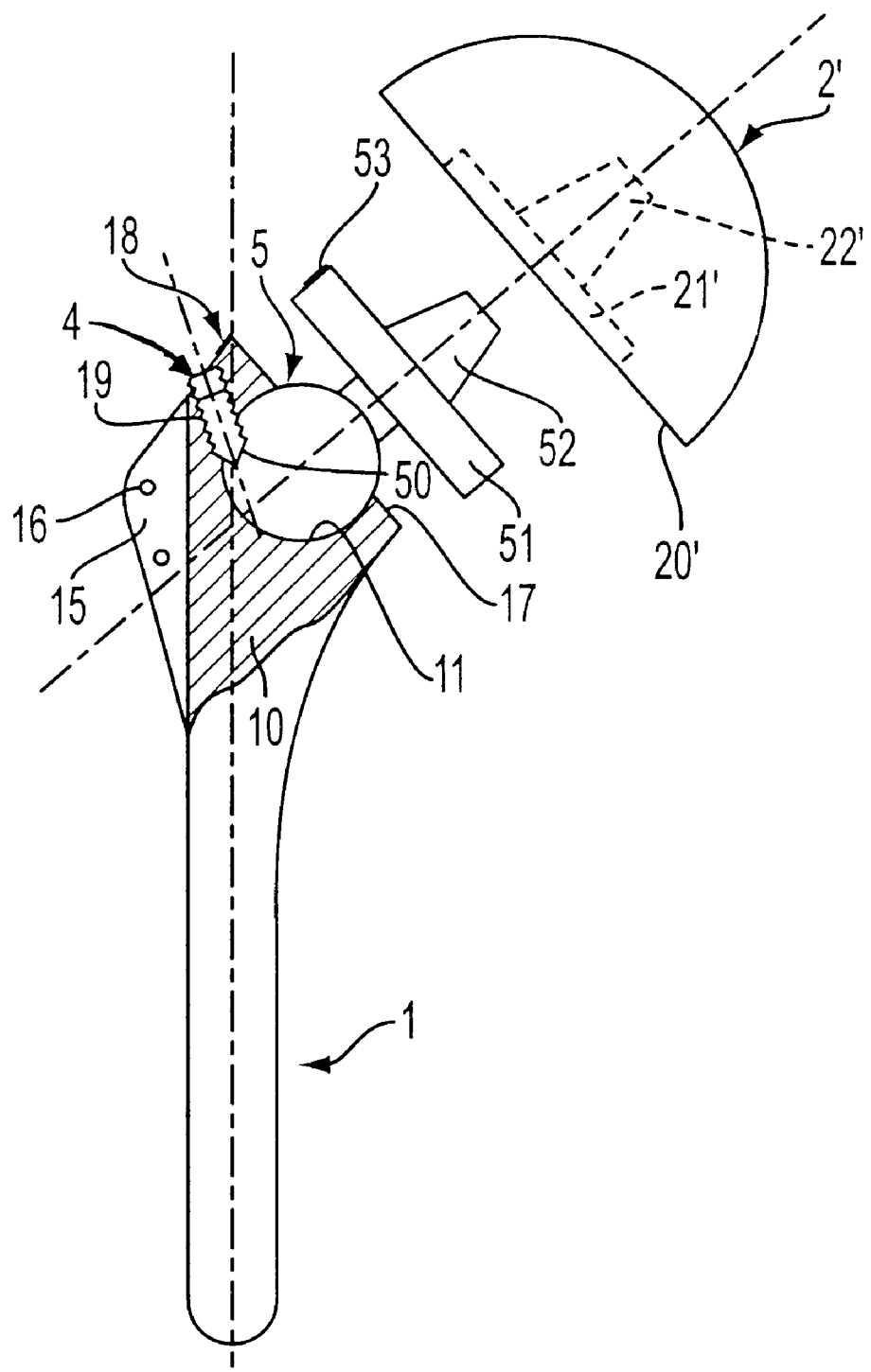
FIG. 7 is a view showing a first alternative form of the humeral prosthesis according to the present invention.

A first alternative form depicted in FIG. 7 consists in the fact that the cavity 11 of the rod 1 receives a sphere 5 which is secured to a circular flange 51, from the center of which there emerges a tapering peg 52. The latter interacts with a hemispherical cup 2' which is similar to those described in patent application No. 2 685 633 of which the applicant is proprietor.

The cup 2' has a base 20' in which there is formed an off-centered circular cavity 21' the diameter of which corresponds, give or take the clearance, to that of the flange 51.

Formed at the center of the cavity 21' is a tapering bore 22' capable of receiving the peg 52. The way in which the cup 2' is mounted and immobilized is identical to the way described in patent application No. 2 685 633.

The screw 4 placed in the hole 19 interacts with recesses 50 made on the surface of the sphere 5 allows it to be immobilized in a determined position. [sic]

Note that the rod 1 comprises the pointer 18 as was described earlier, while the flange 51 comprises reference marks 53.

The combination of a pointer 18 with a reference mark 53 and a recess 50 opposite the axis of the hole 19 reproduces a previously measured combined angular position of the angles α and β measured from the test piece.

Figure 8:
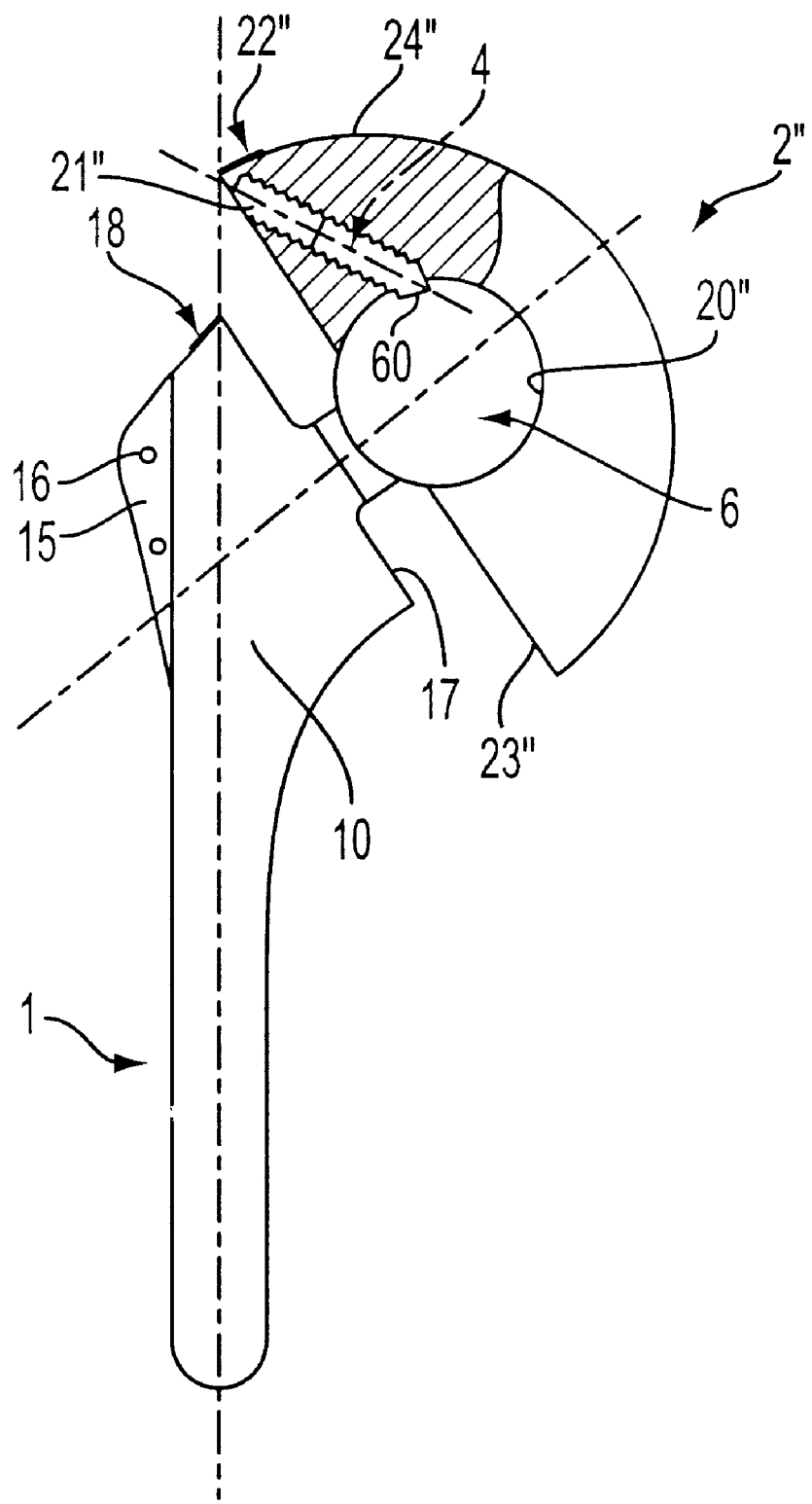
FIG. 8 is a view depicting a second alternative form of the humeral prosthesis according to the present invention.

A second alternative form shown in FIG. 8 consists in the rod 1 being secured at its metaphyseal region 10 to a sphere 6 which extends at right angles to the inclined face 17. The sphere 6 interacts with a cup 2" which has a housing 20" in the shape of a portion of a sphere. A tapped hole 21" passes through the cup 2" to emerge in the housing 20" so that a press screw 4, identical to the one described in FIG. 1, can immobilize the cup on the sphere 6.

The axis of the hole 21" is intended not to run through the center of the housing 20" and/or the sphere 6, so as to allow the latter to be perfectly immobilized in the said housing.

The position of the cup 2" with respect to the rod 1 is determined by the reference marks 22" provided either on the base 23" or on the exterior profile 24" of the cup, of the fixed pointer 18 provided on the rod 1 and of the recesses 60 formed on the surface of the sphere 6.

Note that the combination of a pointer 18 with a reference mark 22" and a recess 60 opposite the axis of the hole 21" reproduces a previously measured combined angular position of the angles α and β measured from the test piece.

Figure 9:
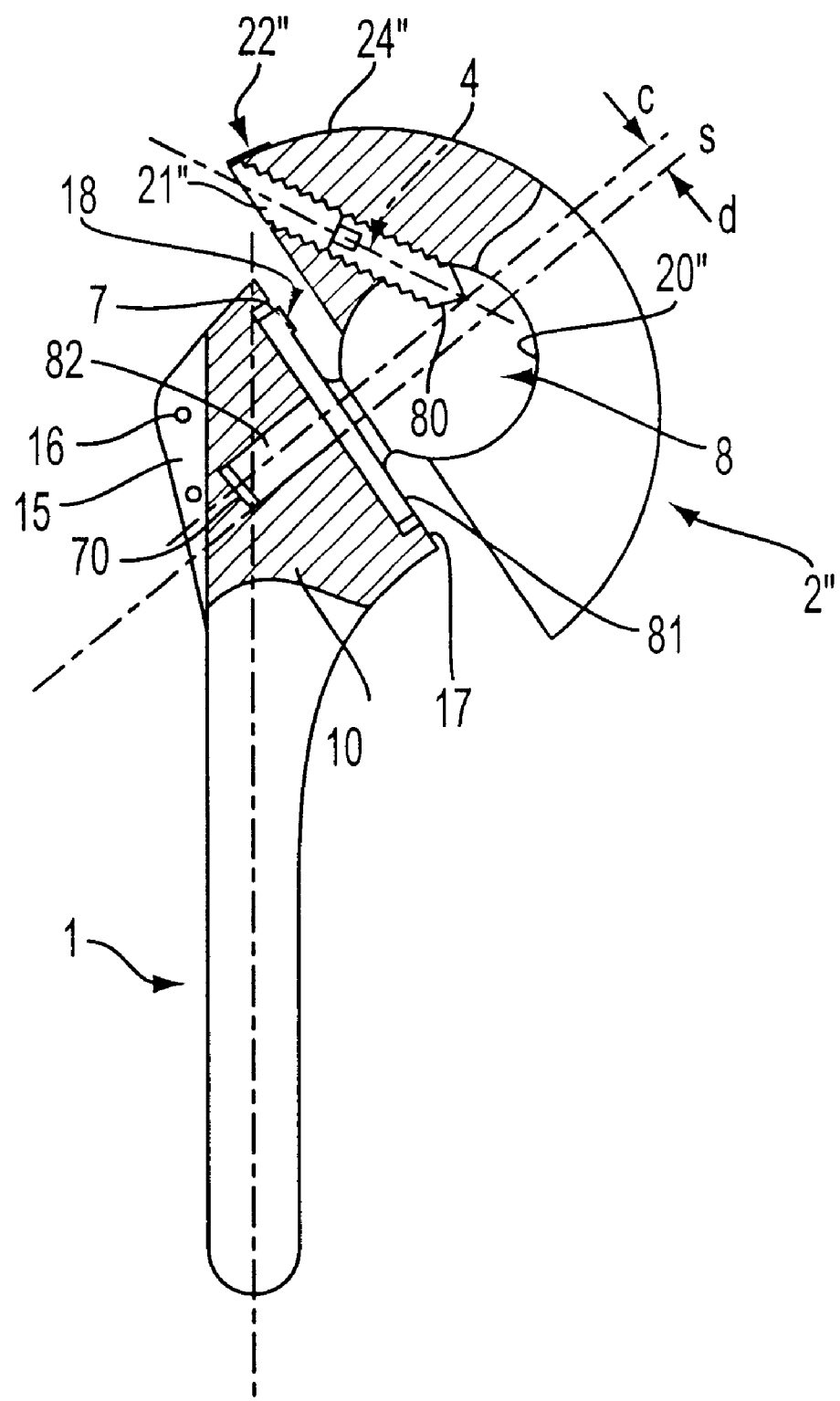
FIG. 9 is a view illustrating a third alternative form of the humeral prosthesis according to the present invention.

A third alternative form illustrated in FIG. 9 consists in the metaphyseal region 10 of the rod 1 comprising on its inclined face 17 a housing 7 in the middle of which there is drilled a non-emerging hole 70 of tapering profile. The housing 7 is intended to receive a flange 81 secured to a tapering peg 82 which interacts with the hole 70 to immobilize the flange 81 on the rod 1 by wedging. The flange 81 has, on the opposite side from the tapering peg 82, a sphere 8 which interacts with the housing 20" of the cup 2" described previously in FIG. 8.

Note that the axis S of the sphere 8 is offset by a distance d with respect to the axis C of the flange 81 fitted without play into the housing 7 of the rod 1 to allow the cup 2" to be offcentered.

The position of the cup 2" with respect to the rod 1 is determined by the reference marks 22" provided either on the base 23" or on the exterior profile 24" of the said cup, of the fixed pointer 18 provided either on the rod 1 or on the flange 81 and of the recesses 80 formed on the surface of the sphere 8.

Note that the combination of a pointer 18 with a reference mark 22" and a recess 80 facing the axis of the hole 21" reproduces a previously measured combined angular position of the angles α and β measured from the test piece.

A fourth alternative form according to the invention, depicted in FIG. 10, consists in the rod 1 being identical to the one described previously in FIG. 1 so that its cavity 11 interacts with a sphere 9 similar to the one described in patent application FR 2 727 002 of which the applicant is proprietor.

The sphere 9 comprises at its middle, a bore 91 into which there opens a radial slot 92. The bore 91 is intended to receive a rod 21''' secured to and laterally offset by a distance d with respect to the middle of the cup 2''', to allow the latter to be offcentered.

The fact that the cup 2''' is independent of the sphere 9 allows heightwise adjustment of the latter with respect to the metaphyseal region 10 of the rod 1.

Note that in this embodiment, the screw 4 interacting with the hole 19 on the one hand allows the sphere 9 to be immobilized in the cavity 11 and on the other hand allows the rod 21''' to be fixed into the bore 91.

Attachment may be supplemented by another binding screw to improve the fixing of the rod 21''' into the bore 91.

The position of the cup 2''' with respect to the rod 1 is determined by the reference marks 93 provided on the truncated poles 94 of the sphere 9, of the fixed pointer 18 provided either on the rod 1 and of the recesses 90 formed on the surface of the sphere 9. [sic]

Note that the combination of a pointer 18 with a reference mark 93 and a recess 90 opposite the axis of the hole 19 reproduces a previously measured combined angular position of the angles α and β measured from the test piece.

The humeral prostheses described hereinabove are set up using a test piece or identical model of the prosthesis to be fitted. This test piece thus allows the surgeon to measure perfectly the relative position of cup/sphere with respect to the rod 1 as a function of two angles α and β. To each combination of its two angles there corresponds a reference mark 20, 53, 22'', 93 to be used on the prostheses to be implanted. The angles α and β are defined with respect to the reference axis which is the axis of the rod or of the humeral canal.

Thus, the angle α is the angle of inclination in the frontal plane, while the angle β is the anteversion or retroversion angle of inclination with respect to the frontal plane about the axis of the rod.

The surgeon transfers the measurements, as far as the tolerances will allow, read off from the test piece onto the humeral prosthesis to be implanted, using the fixed pointer 18, the graduations or reference marks 20, 53, 22'', 93 and the recesses 30, 50, 60, 80, 90 so that the sphere 3, 5, 6, 8, 9 and/or the cup 2, 2', 2'', 2''' will, with respect to the rod 1, be positioned in accordance with the combination of angles α and β.

The surgeon immobilizes the sphere 3, 5, 6, 8, 9 and/or the cup 2, 2', 2'', 2''' in the determined position by means of the binding screw 4 before implanting the prosthesis in the patient's humeral canal.

What is claimed is:

1. A humeral prosthesis comprising:
   a rod for anchoring into a humeral canal of a humerus;
   a hemispherical cup adapted to engage a shoulder socket;
   a connection which connects the rod to the hemispherical cup, the connection comprising a spherical portion;
   the spherical portion comprising a spherical engaging surface having at least one recess;
   at least one reference mark disposed on one of the rod, the hemispherical cup, and the connection, the at least one reference mark corresponding to the at least one recess; and
   a binding mechanism for engaging the at least one recess, wherein the hemispherical cup is pivotal about the spherical portion and is fixable in a finite number of combined angular positions which correspond to a number of recesses.

2. The humeral prosthesis of claim 1, further comprising a fixed pointer disposed on an exterior surface of one of the rod, the hemispherical cup, and the connection,
   wherein the pointer and the at least one reference mark line up when the binding mechanism engages the at least one recess.

3. The humeral prosthesis of claim 1, wherein the rod comprises a pointer disposed on an exterior surface and the hemispherical cup comprises the at least one reference mark disposed on an exterior surface, the pointer and the at least one reference mark lining up when the at least one recess is engaged by the binding mechanism.

4. The humeral prosthesis of claim 3, wherein the rod comprises a cavity which receives the spherical portion and a hole for receiving the binding mechanism.

5. The humeral prosthesis of claim 3, wherein the hemispherical cup comprises a cavity which receives the spherical portion and a hole for receiving the binding mechanism.

6. The humeral prosthesis of claim 1, wherein the binding mechanism engages the at least one recess at an angle which is not perpendicular to a center axis of the spherical portion.

7. The humeral prosthesis of claim 1, wherein the rod comprises a cavity which receives the spherical portion and a hole for receiving the binding mechanism.

8. The humeral prosthesis of claim 1, further comprising a pointer disposed on an exterior surface of the rod, wherein the at least one reference mark is disposed on an exterior surface of the connection.

9. The humeral prosthesis of claim 8, wherein the rod comprises a cavity which receives the spherical portion and at least one hole for receiving the binding mechanism.

10. The humeral prosthesis of claim 8, wherein the connection comprises a tapered peg which engages a tapered bore in the hemispherical cup.

11. The humeral prosthesis of claim 1, further comprising a pointer disposed on an exterior surface of the connection, wherein the hemispherical cup comprises the at least one reference mark, a cavity which receives the spherical portion, and a hole for receiving the binding mechanism.

12. The humeral prosthesis of claim 11, wherein the connection comprises a tapered peg which engages a tapered bore in the rod.

13. The humeral prosthesis of claim 1, wherein the rod comprises a pointer disposed on an exterior surface, the spherical engaging surface comprises a plurality of recesses, and the hemispherical cup comprises a plurality of reference marks disposed on an exterior surface, such that when the binding mechanism engages one of the plurality of recesses, at least one of the plurality of reference marks lines up with the pointer.

14. The humeral prosthesis of claim 13, wherein the spherical portion is integral with the hemispherical cup and the rod comprises a cavity for receiving the spherical portion.

15. The humeral prosthesis of claim 13, wherein the spherical portion is integral with the rod and the hemispherical cup comprises a cavity for receiving the spherical portion.

16. The humeral prosthesis of claim 1, wherein the rod comprises a pointer disposed on an exterior surface, the spherical engaging surface comprises a plurality of recesses, and the connection comprises a plurality of reference marks disposed on an exterior surface, such that when the binding mechanism engages one of the plurality of recesses, at least one of the plurality of reference marks lines up with the pointer.

17. The humeral prosthesis of claim 16, wherein the spherical portion is integral with the connection and the rod comprises a cavity for receiving the spherical portion.

18. The humeral prosthesis of claim 17, wherein the connection comprises a tapered peg which engages a tapered bore in the hemispherical cup.

19. The humeral prosthesis of claim 16, wherein the spherical portion is integral with the connection and the hemispherical cup comprises a cavity for receiving the spherical portion.

20. The humeral prosthesis of claim 19, wherein the connection comprises a tapered peg which engages a tapered bore in the rod.

21. The humeral prosthesis of claim 16, wherein the connection comprises an integrally formed spherical portion which engages a cavity in the rod and an integrally formed tapered peg which engages a tapered bore in the hemispherical cup.

22. The humeral prosthesis of claim 21, wherein a center axis of the spherical portion is offset with respect to a center axis of the tapered peg by a distance.

23. The humeral prosthesis of claim 16, wherein the connection comprises an integrally formed spherical portion which engages a cavity in the hemispherical cup and an integrally formed tapered peg which engages a tapered bore in the rod.

24. The humeral prosthesis of claim 23, wherein a center axis of the spherical portion is offset with respect to a center axis of the tapered peg by a distance.

25. The humeral prosthesis of claim 1, wherein the rod comprises a pointer disposed on an exterior surface, the spherical engaging surface comprises a plurality of recesses, the spherical portion comprises a radial slot and a plurality of reference marks disposed on an exterior surface, and the hemispherical cup comprises a rod which engages the radial slot.

26. The humeral prosthesis of claim 1, wherein when the at least one recess comprises a plurality of recesses and the at least one reference mark comprises a plurality of reference marks.

27. The humeral prosthesis of claim 26, wherein the binding mechanism is engageable with each of the plurality of recess, such that when a recess is engaged by the binding mechanism, one of the plurality of reference marks lines up with a pointer.

28. The humeral prosthesis of claim 1, wherein the binding mechanism comprises a screw.

29. A humeral prosthesis comprising:
a rod for anchoring into a humeral canal of a humerus comprising a pointer disposed on an exterior surface of the rod;
a hemispherical cup adapted to engage a shoulder socket, the hemispherical cup comprising a plurality of reference marks disposed on an exterior surface;
a connection which connects the rod to the hemispherical cup, the connection comprising a spherical portion;
the spherical portion comprising a spherical engaging surface having a plurality of recesses; and
a binding mechanism for engaging at least one of the plurality of recesses, wherein one of the plurality of reference marks lines up with the pointer when the binding mechanism engages one of the plurality of recesses.

30. A humeral prosthesis comprising:
a rod for anchoring into a humeral canal of a humerus comprising a pointer disposed on an exterior surface of the rod;
a hemispherical cup adapted to engage a shoulder socket;
a connection comprising a spherical portion and a plurality of reference marks disposed on an exterior surface;
the spherical portion comprising a spherical engaging surface having a plurality of recesses; and
a binding mechanism for engaging at least one of the plurality of recesses,
wherein one of the plurality of reference marks lines up with the pointer when the binding mechanism engages one of the plurality of recesses.

31. A humeral prosthesis comprising:
a rod for anchoring into a humeral canal of a humerus;
a hemispherical cup adapted to engage a shoulder socket, the hemispherical cup comprising a plurality of reference marks disposed on an exterior surface;
a connection which connects the rod to the hemispherical cup, the connection comprising a spherical portion and a pointer disposed on an exterior surface;
the spherical portion comprising a spherical engaging surface having a plurality of recesses; and
a binding mechanism for engaging at least one of the plurality of recesses,
wherein one of the plurality of reference marks lines up with the pointer when the binding mechanism engages one of the plurality of recesses.

* * * * *